United States Patent
Goepfert et al.

(10) Patent No.: US 10,329,595 B2
(45) Date of Patent: Jun. 25, 2019

(54) CMV PROMOTER AND METHOD FOR PRODUCTION OF POLYPEPTIDES

(71) Applicant: Hoffmann-La Roche Inc., Little Falls, NJ (US)

(72) Inventors: Ulrich Goepfert, Penzberg (DE); Benjamin Moritz, Munich (DE)

(73) Assignee: HOFFMANN-LA ROCHE INC., Little Falls, NJ (US)

(*) Notice: Subject to any disclaimer, the term of this patent is extended or adjusted under 35 U.S.C. 154(b) by 10 days.

(21) Appl. No.: 15/356,091

(22) Filed: Nov. 18, 2016

(65) Prior Publication Data
US 2017/0067087 A1 Mar. 9, 2017

Related U.S. Application Data

(63) Continuation of application No. PCT/EP2015/060880, filed on May 18, 2015.

(30) Foreign Application Priority Data

May 19, 2014 (EP) .................................... 14168901
Nov. 4, 2014 (EP) .................................... 14191705

(51) Int. Cl.
| | | |
|---|---|---|
| C12N 15/85 | (2006.01) | |
| C12P 21/00 | (2006.01) | |
| C12N 7/00 | (2006.01) | |
| C07K 16/00 | (2006.01) | |

(52) U.S. Cl.
CPC .............. *C12P 21/00* (2013.01); *C07K 16/00* (2013.01); *C12N 7/00* (2013.01); *C12N 15/85* (2013.01); *C07K 2317/14* (2013.01); *C12N 2710/16122* (2013.01); *C12N 2710/16143* (2013.01); *C12N 2800/107* (2013.01); *C12N 2830/46* (2013.01); *C12N 2830/60* (2013.01)

(58) Field of Classification Search
None
See application file for complete search history.

(56) References Cited

FOREIGN PATENT DOCUMENTS

| WO | WO-2011054519 A1 * | 5/2011 | .............. C07K 16/00 |
|---|---|---|---|
| WO | 2012/099540 A1 | 7/2012 | |

OTHER PUBLICATIONS

Result 4 of N_Geneseq_201804 sequence search (Year: 2011).*
ISR and Written Opinion for PCT/EP2015/060880.
Kim et al., "Stability of Protein Production From Recombinant Mammalian Cells" Biotechnol. Bioeng. 108:2434-2446 ( 2011).
Brooks et al., "Transcriptional silencing is associated with extensive methylation of the CMV promoter following adenoviral gene delivery to muscle" The Journal of Gene Medicine 6:395-404 ( 2004).
Hsu et al., "Targeted methylation of CMV and E1A viral promoters" Biochemical and Biophysical Research Communications 402:228-234 ( 2010).
ISR and Written Opinion for PCT/EP2015/060880, dated Sep. 16, 2015, 17 pages.
Mariati et al., "Insertion of Core CpG Island Element into Human CMV Promoter for Enhancing Recombinant Protein Expression Stability in CHO Cells" Biotechnol. Prog. 30(3):523-534 ( 2014).
Osterlehner et al., "Promoter Methylation and Transgene Copy Numbers Predict Unstable Protein Production in Recombinant Chinese Hamster Ovary Cell Lines" Biotechnology and Bioengineering 108(11):2670-2681 ( 2011).
Proesch et al., "Inactivation of the very strong HCMV immediate early promoter by DNA CPG methylation in vitro" Biological Chemistry Hoppe-Seyler (XP001029311), 377:195-201 (Mar. 1996).
Yang et al., "DNA methylation contributes to loss in productivity of monoclonal antibody-producing CHO cell lines" Journal of Biotechnology 147:180-185 ( 2010).

* cited by examiner

*Primary Examiner* — Jennifer Dunston
(74) *Attorney, Agent, or Firm* — Genentech, Inc.

(57) ABSTRACT

The current invention reports a promoter that has the nucleic acid sequence of SEQ ID NO: 02 or SEQ ID NO: 03 which is a human CMV major immediate-early (hCMV-MIE) promoter/enhancer with C to G point mutation at position −41 and/or −179 relative to the transcription start site. This new promoter is especially useful for the production of polypeptides at large scale as it shows reduced promoter silencing and improved polypeptide production.

13 Claims, 12 Drawing Sheets

Specification includes a Sequence Listing.

A)

B)

A)

B)

SEQUENCE LISTING

<160> NUMBER OF SEQ ID NOS: 6

<210> SEQ ID NO 1
<211> LENGTH: 601
<212> TYPE: DNA
<213> ORGANISM: Homo sapiens

<400> SEQUENCE: 1

```
gttgacattg attattgact agttattaat agtaatcaat tacggggtca ttagttcata    60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtacgcccc ctattgacgt caatgacggt aaatggcccg   300
cctggcatta tgcccagtac atgaccttat gggactttcc tacttggcag tacatctacg   360
tattagtcat cgctattagc atggtgatgc ggttttggca gtacatcaat gggcgtggat   420
agcggtttga ctcacgggga tttccaagtc tccaccccat tgacgtcaat gggagtttgt   480
tttggcacca aaatcaacgg gactttccaa aatgtcgtaa caactccgcc ccattgacgc   540
aaatgggcgg taggcgtgta cggtgggagg tctatataag cagagctccg tttagtgaac   600
g                                                                   601
```

<210> SEQ ID NO 2
<211> LENGTH: 601
<212> TYPE: DNA
<213> ORGANISM: Artificial Sequence
<220> FEATURE:
<223> OTHER INFORMATION: hCMV-MIE mutant

<400> SEQUENCE: 2

```
gttgacattg attattgact agttattaat agtaatcaat tacggggtca ttagttcata    60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
```

```
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattagc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta gggtgggagg tctatataag cagagctccg tttagtgaac    600
g                                                                   601

<210> SEQ ID NO 3
<211> LENGTH: 601
<212> TYPE: DNA
<213> ORGANISM: Artificial Sequence
<220> FEATURE:
<223> OTHER INFORMATION: hCMV-MIE mutant

<400> SEQUENCE: 3
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattagc atggtgatgc ggttttggca gtacatcaat gggcgtggat    420
aggggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctccg tttagtgaac    600
g                                                                   601

<210> SEQ ID NO 4
<211> LENGTH: 876
<212> TYPE: DNA
<213> ORGANISM: Artificial Sequence
<220> FEATURE:
<223> OTHER INFORMATION: eGFP

<400> SEQUENCE: 4
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
```

```
tacctgagca cccagtccgc cctgagcaaa gaccccaacg agaagcgcga tcacatggtc    660
ctgctggagt tcgtgaccgc cgccgggatc actctcggca tggacgagct gtacaagtcc    720
ggactcagat ctcgagctca agcttcgaat tctgcagtcg acggtaccgc gggcccggga    780
tccaccggat ctagacatgg cttcccgccg gaggtggagg agcaggatga tggcacgctg    840
cccatgtctt gtgcccagga gagcgggatg gaccgt                              876
```

<210> SEQ ID NO 5
<211> LENGTH: 1524
<212> TYPE: DNA
<213> ORGANISM: Homo sapiens

<400> SEQUENCE: 5

```
atgggatgga gctgtatcat cctcttcttg gtagcaacag ctacaggtgt ccactccatc     60
atcccagttg aggaggagaa tccggacttc tggaaccgcg aggcagccga ggccctgggt    120
gccgccaaga agctgcagcc tgcacagaca gccgccaaga acctcatcat cttcctgggc    180
gatgggatgg gggtgtctac ggtgacagct gccaggatcc taaaagggca gaagaaggac    240
aaactggggc ctgagatacc cctggccatg gaccgcttcc catatgtggc tctgtccaag    300
acatacaatg tagacaaaca tgtgccagac agtggagcca cagccacggc ctacctgtgc    360
ggggtcaagg gcaacttcca gaccattggc ttgagtgcag ccgcccgctt taaccagtgc    420
aacacgacac gcggcaacga ggtcatctcc gtgatgaatc gggccaagaa agcagggaag    480
tcagtgggag tggtaaccac cacacgagtg cagcacgcct cgccagccgg cacctacgcc    540
cacacggtga accgcaactg gtactcggac gccgacgtgc ctgcctcggc ccgccaggag    600
gggtgccagg acatcgctac gcagctcatc tccaacatgg acattgacgt gatcctaggt    660
ggaggccgaa agtacatgtt tcgcatggga accccagacc ctgagtaccc agatgactac    720
agccaaggtg ggaccaggct ggacgggaag aatctggtgc aggaatggct ggcgaagcgc    780
cagggtgccc ggtatgtgtg gaaccgcact gagctcatgc aggcttccct ggacccgtct    840
gtgacccatc tcatgggtct cttttgagcct ggagacatga aatacgagat ccaccgagac    900
tccacactgg acccctccct gatggagatg acagaggctg ccctgcgcct gctgagcagg    960 aaccccgcg cgcttcttcct cttcgtggag ggtggtcgca tcgaccatgg tcatcatgaa   1020
agcagggctt accgggcact gactgagacg atcatgttcg acgacgccat tgagagggcg   1080
ggccagctca ccagcgagga ggacacgctg agcctcgtca ctgccgacca ctcccacgtc   1140
ttctccttcg gaggctaccc cctgcgaggg agctccatct tcgggctggc ccctggcaag   1200
gcccgggaca ggaaggccta cacggtcctc ctatacggaa acggtccagg ctatgtgctc   1260
aaggacggcg cccggccgga tgttaccgag agcgagagcg ggagcccga gtatcggcag   1320 cagtcagcag tgcccctgga cgaagagacc cacgcaggcg aggacgtggc ggtgttcgcg   1380
cgcggcccgc aggcgcacct ggttcacggc gtgcaggagc agaccttcat agcgcacgtc   1440
atggccttcg ccgcctgcct ggagccctac accgcctgcg acctggcgcc cccgccggc   1500 accaccgacg ccgcgcaccc gggt                                          1524
```

<210> SEQ ID NO 6
<211> LENGTH: 601
<212> TYPE: DNA
<213> ORGANISM: Artificial Sequence
<220> FEATURE:
<223> OTHER INFORMATION: hCMV-MIE mutant

<400> SEQUENCE: 6

-continued

```
gttgacattg attattgact agtgattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattagc atggtgatgc ggttttggca gtacatcaat gggcgtggat     420
aggggtttga ctcacgggga tttccaagtc tccacccat tgacgtcaat gggagtttgt     480
tttggcacca aaatcaacgg gactttccaa aatgtcgtaa caactccgcc ccattgacgc     540
aaatgggcgg taggcgtgta gggtgggagg tctatataag cagagctccg tttagtgaac     600
g                                                                    601
```

CMV PROMOTER AND METHOD FOR PRODUCTION OF POLYPEPTIDES

CROSS REFERENCE TO RELATED APPLICATIONS

This application claims priority to PCT Application No. PCT/EP2015/060880, filed on May 18, 2015, which claims priority to European patent application no. 14168901.8, filed on May 19, 2014, and 14191705.4, filed on Nov. 4, 2014 the entire contents of which is incorporated herein by reference.

SUBMISSION OF SEQUENCE LISTING ON ASCII TEXT FILE

The instant application contains a Sequence Listing which has been submitted electronically in ASCII format and is hereby incorporated by reference in its entirety. Said ASCII copy, created on May 13, 2015, is named P32141-US_SeqListing.txt and is 7,523 bytes in size.

BACKGROUND OF THE INVENTION

The current invention is in the field of protein expression. Herein reported is a promotor with at least one point mutation and a method that uses this promoter to produce a polypeptide.

The expression of proteins is a fundamental process in living cells. All information required for protein expression is provided by a single nucleic acid. This nucleic acid not only contains the information of the protein's amino acid sequence, it also provides the regulatory information required (e.g. the ribosomal binding site, the start and end-signals for transcription, splice signals, enhancer elements, etc.) including a promoter/promoter sequence.

A promoter is a nucleic acid that regulates the amount of transcription of a nucleic acid, e.g. encoding a polypeptide, to which it is operably linked, into pre-mRNA. It is a transcription control element, which is located around the RNA polymerase initiation site at the 5'-end of an operably linked coding sequence. From analysis of the SV40 early promoter it is known that recognition/binding sites for transcription activators are contained in promoters in segments consisting of 7-20 basepairs. One segment is the start site for RNA synthesis, e.g. the well known TATA-box. Other segments, located approximately 30-110 basepairs 5', i.e. upstream, to the start site for RNA synthesis, are defining the frequency of transcription initiation. A promoter at least requires one segment that initiates RNA synthesis at a specific site and in a defined direction, i.e. in 5' to 3' direction.

The gradual loss of productivity in long-term culture is a common issue with the development of manufacturing cell lines (Barnes, L. M., et al. Biotechnol. Bioeng. 81 (2003) 631-639). The decrease of recombinant protein expression can be due to a loss of transgene copies and/or silencing of the transgene promoter (see e.g. Escher, G., et al. J. Lipid Res. 46 (2005) 356-365; Krishnan, M., et al., FASEB J. 20 (2006) 106-108; Yang, Y., et al., J. Biotechnol. 147 (2010) 180-185). Silencing of promoters is caused by epigenetic modifications of chromatin such as posttranslational modifications of histones as well as direct methylation of promoter DNA at CpG sites (see e.g. Cedar, H. and Bergman, Y., Nat. Rev. Genet. 10 (2009) 295-304; De Carvalho, D. D. et al., Trends Cell Biol 20 (2010): 609-617; Klose; R. J. and Bird, A. P., Trends Biochem Sci 31 (2006): 89-97). Methylated promoters are in general inactive.

The very strong promoter and enhancer of the major immediate-early genes of the human cytomegalovirus (hCMV-MIE) is used for the recombinant expression of polypeptides in mammalian cells. It has been shown that the promoter is prone to silencing by methylation in transient as well as stably transfected mammalian cells (see e.g. Escher, G., et al. J. Lipid Res. 46 (2005) 356-365; Krishnan, M., et al., FASEB J. 20 (2006) 106-108; Proesch, S. et al., Biol Chem Heppe Seyler 377 (1996): 195-201; Yang, Y., et al., J. Biotechnol. 147 (2010) 180-185).

It has been demonstrated previously in WO 2011/128377 that direct methylation of the hCMV-MIE promoter can be used as early marker to predict production instability of recombinant CHO cell lines.

Osterlehner, A., et al., report promoter methylation and trans gene copy numbers predict unstable protein production in recombinant Chinese hamster ovary cell lines and describe that the different CpG sites are methylated with different frequency (Biotechnol. Bioeng. 108 (2011) 2670-2681).

SUMMARY OF THE INVENTION

It has been found that a C to G point mutation, i.e. a single C to G mutation, in the hCMV-MIE promoter at specific sites results in reduced promoter silencing and likewise in improved production stability. In addition, it has been found that higher titers of produced polypeptide can be achieved. Mutation of C to G at position −41 and/or at position −179 relative to the transcription start site have shown to be particularly effective.

One aspect as reported herein is a human CMV promoter (based on the promoter of SEQ ID NO: 01) that has at nucleotide position −41 (and/) or −179 relative to the transcription start site the nucleotide G.

In one embodiment of this aspect the human CMV promoter has improved production stability and/or improved product titer (when compared to human CMV promoters without C to G point mutations at position −41 and/or −179 relative to the transcriptions start site).

In one embodiment of this aspect the human CMV promoter has the nucleic acid sequence of SEQ ID NO: 02 or SEQ ID NO: 03.

One aspect as reported herein is a promoter that has the nucleic acid sequence of SEQ ID NO: 02.

One aspect as reported herein is a nucleic acid characterized in that it is consisting of the nucleic acid of SEQ ID NO: 02 and has a promoter strength of at least 80% of the human CMV major immediate-early promoter of SEQ ID NO: 01 when operably linked to the nucleic acid of SEQ ID NO: 04 encoding the enhanced green fluorescent protein (eGFP).

One aspect as reported herein is a method for the production of a polypeptide, characterized in that it comprises the following steps:

a) transfecting a eukaryotic cell with a nucleic acid comprising an expression cassette comprising a first nucleic acid of SEQ ID NO: 02 operably linked to a second nucleic acid encoding the polypeptide,
b) selecting a cell transfected in step a),
c) cultivating the selected cell of step b) (under conditions suitable for the expression of the polypeptide),
d) recovering the polypeptide from the cell or the cultivation medium, and thereby producing the polypeptide.

In one embodiment of this aspect the production is a production at large scale. In one embodiment the production is at a final cultivation volume of 500 l or more, in one embodiment of 500 l to 10,000 l.

In one embodiment of this aspect said polypeptide is an immunoglobulin, or an immunoglobulin-fragment, or an immunoglobulin-conjugate.

In one embodiment of this aspect the polypeptide is an immunoglobulin light chain or an immunoglobulin heavy chain or a variant thereof or a fragment thereof or a fusion thereof.

In one embodiment of this aspect the nucleic acid comprises a further expression cassette encoding a selectable marker. In one embodiment of this aspect the nucleic acid comprises a further expression cassette encoding a immunoglobulin light chain or an immunoglobulin heavy chain.

In one embodiment of this aspect said eukaryotic cell is a mammalian cell.

In one embodiment of this aspect said mammalian cell is a CHO cell, a BHK cell, a HEK cell, a Sp2/0 cell or a Per.C6® cell.

In one embodiment of this aspect said mammalian cell is a CHO cell or a HEK cell.

In one embodiment of this aspect said selectable marker is a dihydrofolate reductase, an aminoglycoside phosphotransferase or a hygromycin-phosphotransferase.

One aspect as reported herein is the use of a promoter of SEQ ID NO: 02 for the production of a polypeptide.

One aspect as reported herein is a cell comprising the promoter as reported herein or the nucleic acid as reported herein.

One aspect as reported herein is a promoter that has the nucleic acid sequence of SEQ ID NO: 03

One aspect as reported herein is a nucleic acid characterized in that it is consisting of the nucleic acid of SEQ ID NO: 03 and has a promoter strength of at least 80% of the human CMV major immediate-early promoter of SEQ ID NO: 01 when operably linked to the nucleic acid of SEQ ID NO: 04 encoding the enhanced green fluorescent protein (eGFP).

One aspect as reported herein is a method for the production of a polypeptide, characterized in that it comprises the following steps:
  a) transfecting a eukaryotic cell with a nucleic acid comprising an expression cassette comprising a first nucleic acid of SEQ ID NO: 03 operably linked to a second nucleic acid encoding the polypeptide,
  b) selecting a cell transfected in step a),
  c) cultivating the selected cell of step b) (under conditions suitable for the expression of the polypeptide),
  d) recovering the polypeptide from the cell or the cultivation medium,
and thereby producing the polypeptide.

In one embodiment of this aspect the production is a production at large scale. In one embodiment the production is at a final cultivation volume of 500 l or more, in one embodiment of 500 l to 10,000 l.

In one embodiment of this aspect said polypeptide is an immunoglobulin, or an immunoglobulin-fragment, or an immunoglobulin-conjugate.

In one embodiment of this aspect the polypeptide is an immunoglobulin light chain or an immunoglobulin heavy chain or a variant thereof or a fragment thereof or a fusion thereof.

In one embodiment of this aspect the nucleic acid comprises a further expression cassette encoding a selectable marker. In one embodiment of this aspect the nucleic acid comprises a further expression cassette encoding a immunoglobulin light chain or an immunoglobulin heavy chain.

In one embodiment of this aspect said eukaryotic cell is a mammalian cell.

In one embodiment of this aspect said mammalian cell is a CHO cell, a BHK cell, a HEK cell, a Sp2/0 cell or a Per.C6® cell.

In one embodiment of this aspect said mammalian cell is a CHO cell or a HEK cell.

In one embodiment of this aspect said selectable marker is a dihydrofolate reductase, an aminoglycoside phosphotransferase or a hygromycin-phosphotransferase.

One aspect as reported herein is the use of a promoter of SEQ ID NO: 03 for the production of a polypeptide.

One aspect as reported herein is a cell comprising the promoter as reported herein or the nucleic acid as reported herein.

One aspect as reported herein is a human CMV promoter that has at nucleotide position −41 relative to the transcription start site the nucleotide G.

In one embodiment of this aspect the human CMV promoter is a human CMV major immediate-early promoter.

One aspect as reported herein is a human CMV promoter that has at nucleotide position −179 relative to the transcription start site the nucleotide G.

In one embodiment of this aspect the human CMV promoter is a human CMV major immediate-early promoter.

DETAILED DESCRIPTION OF THE INVENTION

Figure 1:
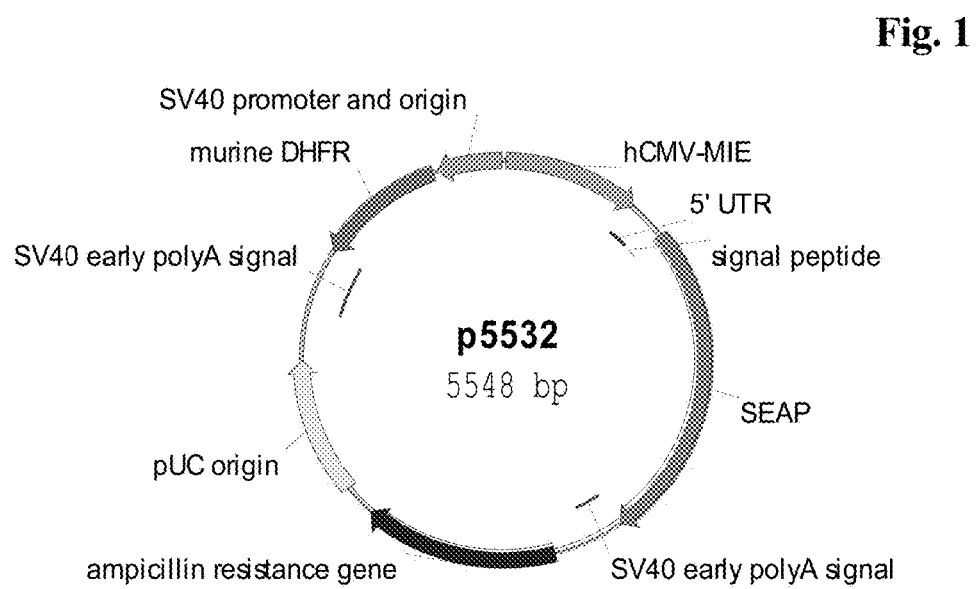
FIG. 1 Plasmid map of secreted alkaline phosphatase (SEAP) expressing plasmid p5532

When using stably transfected eukaryotic cell lines for the production/expression of recombinant polypeptides, like secreted proteins, an intracellular reporterprotein or a cell surface marker, the gradual loss of productivity in long-term culture is a common issue with the development of manufacturing cell lines (Barnes, L. M., et al. Biotechnol. Bioeng. 81 (2003) 631-639). For production cell lines/cell clones, i.e. cell clone/cell lines that are to be used for the large scale recombinant production of a polypeptide, such as e.g. an antibody, the production stability, i.e. the loss of productivity generation by generation, of the cell clone/cell line is important. Thus, mammalian cell lines for recombinant protein production need to maintain productivity over extended cultivation times. Generally the production stability of a cell clone/cell line is determined by cultivating the cell clone/cell line over a long period of time. At regular intervals the medium is diluted with fresh medium and the specific productivity per cell is determined based on the product titer and the viable cell density. The change (normally a reduction) of the specific productivity is indicative of long term production stability of the cell clone/cell line.

The decrease of recombinant protein expression can be due to a loss of transgene copies and/or silencing of the transgene promoter (see e.g. Escher, G., et al. J. Lipid Res. 46 (2005) 356-365; Krishnan, M., et al., FASEB J. 20 (2006) 106-108; Yang, Y., et al., J. Biotechnol. 147 (2010) 180-185). Silencing of promoters is caused by epigenetic modifications of chromatin such as posttranslational modifications of histones as well as direct methylation of promoter DNA at CpG sites (see e.g. Cedar, H. and Bergman, Y., Nat. Rev. Genet. 10 (2009) 295-304; De Carvalho, D. D. et al., Trends Cell Biol 20 (2010): 609-617; Klose; R. J. and Bird, A. P., Trends Biochem Sci 31 (2006): 89-97). Methylated promoters are in general inactive.

It has been shown earlier by Osterlehner, A., et al., that promoter methylation and trans gene copy numbers predict unstable protein production in recombinant Chinese hamster ovary cell lines and describe that the different CpG sites are methylated with different frequency (Biotechnol. Bioeng. 108 (2011) 2670-2681).

Herein different CpG sites were investigated alone or in combination. Various cells lines containing CpG point mutations within the human CMV major immediate-early promoter/enhancer were generated and tested for long term productivity.

It is important that mutations in promoters do not significantly influence its potency of gene expression, i.e. the promoter strength should not be influenced.

It has been found in the current invention that promoter strength is not influenced in hCMV-MIE promoter with the point mutations done as reported herein. No significant differences between plasmids with point mutation in human CMV major immediate-early promoter/enhancer fragment and the unmutated control plasmid could be detected.

The invention is at least in part based on the finding that silencing of promoters can be reduced by point mutations from C to G at specific CpG sites of the human CMV major immediate-early promoter/enhancer. Thereby long-term production stability of cell lines can be improved and recombinant polypeptides can be produced over a long period of time at high/higher yields.

Exemplary CHO cells were stably transfected with plasmid 16107 (with point mutation C-179 to G) or plasmid 16109 (with point mutation C-41 to G) and cultivated. eGFP intensities of 8-10 independent stably transfected cell pools per plasmid were determined over extended cultivation time.

A statistically significant difference in long-term productivity of transfected cells was detected between cells that had been transfected either with plasmid 16109 or control plasmid 16111 (p-values<0.05; see Table below).

It has been found that a positive effect on the stability of reporter gene expression can be achieved when a point mutation of C to G at position −41 relative to the transcription start site is introduced, i.e. the methylation site is eliminated.

TABLE p-values of fluorescence geometrical means of CHO cell pools transfected with plasmid 16107, 16109 or 16111 for the least significant difference (LSD)

| | p-values for LSD of Dunnett's method at date (day of transfection Jan. 28, 2014): | | | | | |
|---|---|---|---|---|---|---|
| plasmid | Mar. 3 | Mar. 7 | Mar. 14 | Mar. 25 | Apr. 7 | Apr. 25 |
| 16109 | 0.0524 | 0.0244* | 0.0273* | 0.0448* | 0.0812 | 0.1044 |
| 16107 | 0.8759 | 0.8006 | 0.8739 | 0.9792 | 1.0 | 0.9965 |
| 16111 | 1.0 | 1.0 | 1.0 | 1.0 | 1.0 | 1.0 |

Thus, one aspect as reported herein is a promoter that has the nucleic acid sequence of SEQ ID NO: 02, i.e. a hCMV-MIE promoter with C-41 to G point mutation. In one embodiment the promoter has at least one point mutation of C to G. In one embodiment the promoter has at two point mutations of C to G. In one embodiment the promoter has at three point mutations of C to G. In one preferred embodiment the promoter has a single point mutation from C to G. In one preferred embodiment the promoter has a single point mutation from C to G at position −41 relative to the transcription start site. In one preferred embodiment the promoter has a single point mutation from C to G at position −179 relative to the transcription start site.

Another aspect as reported herein is a nucleic acid characterized in that it is consisting of the nucleic acid of SEQ ID NO: 02 and has a promoter strength of at least 80% of the human CMV major immediate-early promoter of SEQ ID NO: 01 when operably linked to the nucleic acid of SEQ ID NO: 04 encoding the enhanced green fluorescent protein (eGFP).

One aspect as reported herein is a method for the production of a polypeptide, characterized in that it comprises the following steps:
 a) transfecting a eukaryotic cell with a nucleic acid comprising an expression cassette comprising a first nucleic acid of SEQ ID NO: 02 (i.e. a hCMV-MIE promoter with C-41 to G point mutation) operably linked to a second nucleic acid encoding the polypeptide,
 b) selecting a cell transfected in step a),
 c) cultivating the selected cell of step b) (under conditions suitable for the expression of the polypeptide), d) recovering the polypeptide from the cell or the cultivation medium, and thereby producing the polypeptide.

In one embodiment of this aspect the production is a production at large scale. In one embodiment the production is at a final cultivation volume of 500 l or more, in one embodiment of 500 l to 10,000 l.

In one embodiment of this aspect said polypeptide is an immunoglobulin, or an immunoglobulin-fragment, or an immunoglobulin-conjugate.

In one embodiment of this aspect the polypeptide is an immunoglobulin light chain or an immunoglobulin heavy chain or a variant thereof or a fragment thereof or a fusion thereof. It is understood that it is necessary to include a further expression cassette with a nucleic acid encoding the respective other immunoglobulin chain if a complete immunoglobulin molecule is to be produced. For example, if the polypeptide is an immunoglobulin light chain, a further expression cassette with a nucleic acid encoding an immunoglobulin heavy chain is introduced. In one embodiment of this aspect the nucleic acid comprises a further expression cassette encoding a immunoglobulin light chain or an immunoglobulin heavy chain.

In one embodiment of this aspect the nucleic acid comprises a further expression cassette encoding a selectable marker. In one embodiment of this aspect said selectable marker is a dihydrofolate reductase, an aminoglycoside phosphotransferase or a hygromycin-phosphotransferase.

Another aspect as reported herein is the use of a promoter of SEQ ID NO: 02 for the production of a polypeptide.

In one embodiment of this aspect said eukaryotic cell is a mammalian cell. In one embodiment of this aspect said mammalian cell is a CHO cell, a BHK cell, a HEK cell, a Sp2/0 cell or a Per.C6® cell. In one embodiment of this aspect said mammalian cell is a CHO cell or a HEK cell.

Additionally cell lines 16107 and 16111 were compared directly. The tendency of cvell line 16107 for higher eGFP expression compared to control cell line 16111 show a positive effect of the C to G point mutation at position C-179 relative to the transcription start site on the stability of eGFP expression gene.

Position −41 relative to the transcription start site corresponds to position 561 of SEQ ID NO: 01. Position −179 relative to the transcription start site corresponds to position 423 of SEQ ID NO: 01.

Thus, one aspect as reported herein is a promoter that has the nucleic acid sequence of SEQ ID NO: 03, i.e. a hCMV-MIE promoter with C-179 to G point mutation.

Another aspect as reported herein is a nucleic acid characterized in that it is consisting of the nucleic acid of SEQ ID NO: 03 and has a promoter strength of at least 80% of the human CMV-major immediate-early promoter of SEQ ID NO: 01 when operably linked to the nucleic acid of SEQ ID NO: 04 encoding the enhanced green fluorescent protein (eGFP).

Another aspect as reported herein is a method for the production of a polypeptide, characterized in that it comprises the following steps:
 a) transfecting a eukaryotic cell with a nucleic acid comprising an expression cassette comprising a first nucleic acid of SEQ ID NO: 03 operably linked to a second nucleic acid encoding the polypeptide,
 b) selecting a cell transfected in step a),
 c) cultivating the selected cell of step b) (under conditions suitable for the expression of the polypeptide),
 d) recovering the polypeptide from the cell or the cultivation medium, and thereby producing the polypeptide.

In one embodiment of this aspect the production is a production at large scale. In one embodiment the production is at a final cultivation volume of 500 l or more, in one embodiment of 500 l to 10,000 l.

In one embodiment of this aspect said polypeptide is an immunoglobulin, or an immunoglobulin-fragment, or an immunoglobulin-conjugate.

In one embodiment of this aspect the polypeptide is an immunoglobulin light chain or an immunoglobulin heavy chain or a variant thereof or a fragment thereof or a fusion thereof.

In one embodiment of this aspect the nucleic acid comprises a further expression cassette encoding a selectable marker.

In one embodiment of this aspect said eukaryotic cell is a mammalian cell.

In one embodiment of this aspect said mammalian cell is a CHO cell, a BHK cell, a HEK cell, a Sp2/0 cell or a Per.C6® cell.

In one embodiment of this aspect said mammalian cell is a CHO cell or a HEK cell.

In one embodiment of this aspect said selectable marker is a dihydrofolate reductase, an aminoglycoside phosphotransferase or a hygromycin-phosphotransferase.

Another aspect as reported herein is the use of a promoter of SEQ ID NO: 03 for the production of a polypeptide.

Definitions

A "promoter" refers to a nucleic acid, i.e. polynucleotide sequence, which controls transcription of a nucleic acid to which it is operably linked. A promoter may include signals for RNA polymerase binding and transcription initiation. The promoter(s) used will be functionable in the cell type of the host cell in which expression of the operably linked nucleic acid is contemplated. A large number of promoters including constitutive, inducible, and repressible promoters from a variety of different sources are well known in the art (and identified in databases such as GENBANK). They are available as or within cloned polynucleotides (from, e.g., depositories such as ATCC as well as other commercial or individual sources). A "promoter" comprises a nucleotide sequence that directs the transcription of e.g. an operably linked structural gene. Typically, a promoter is located in the 5' non-coding or 5'-untranslated region (5'UTR) of a gene, proximal to the transcriptional start site of a structural gene. Sequence elements within promoters that function in the initiation of transcription are often characterized by consensus nucleotide sequences. These sequence elements include RNA polymerase binding sites, TATA sequences, CAAT sequences, differentiation-specific elements (DSEs; McGehee, R. E., et al., Mol. Endocrinol. 7 (1993) 551), cyclic AMP response elements (CREs), serum response elements (SREs; Treisman, R., Seminars in Cancer Biol. 1 (1990) 47), glucocorticoid response elements (GREs), and binding sites for other transcription factors, such as CRE/ATF (O'Reilly, M. A., et al., J. Biol. Chem. 267 (1992) 19938), AP2 (Ye, J., et al., J. Biol. Chem. 269 (1994) 25728), SP1, cAMP response element binding protein (CREB; Loeken, M. R., Gene Expr. 3 (1993) 253-264) and octamer factors (see, in general, Watson et al., eds., Molecular Biology of the Gene, 4th ed., The Benjamin/Cummings Publishing Company, Inc. 1987, and Lemaigre, F. P. and Rousseau, G. G., Biochem. J. 303 (1994) 1-14). If a promoter is an inducible promoter, then the rate of transcription increases in response to an inducing agent. In contrast, the rate of transcription is not regulated by an inducing agent if the promoter is a constitutive promoter. Repressible promoters are also known. For example, the c-fos promoter is specifically activated upon binding of growth hormone to its receptor on the cell surface. Tetracycline (tet) regulated expression can be achieved by artificial hybrid promoters that consist e.g. of a CMV promoter followed by two Tet-operator sites. The Tet-repressor binds to the two Tet-operator sites and blocks transcription.

Upon addition of the inducer tetracycline, the Tet-repressor is released from the Tet-operator sites and transcription proceeds (Gossen, M. and Bujard, H., Proc. Natl. Acad. Sci. USA 89 (1992) 5547-5551). For other inducible promoters including metallothionein and heat shock promoters, see, e.g., Sambrook, et al. (supra), and Gossen, M., et al., Curr. Opin. Biotech. 5 (1994) 516-520. Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-1, see e.g. U.S. Pat. No. 5,888,809), human EF-1 alpha, ubiquitin, and human cytomegalovirus major immediate-early promoter (CMV-MIE). An "enhancer" (i.e., a cis-acting DNA element that acts on a promoter to increase transcription) may be necessary to function in conjunction with the promoter to increase the level of expression obtained with a promoter alone, and may be included as a transcriptional regulatory element. Often, the polynucleotide segment containing the promoter will include enhancer sequences as well (e.g., CMV or SV40).

The term "CpG-site" denotes the dinucleotide CG within a nucleic acid that can be recognized by the methylating enzymes of a cell and wherein the cytosine can be converted to 5-methyl cytosine. In one embodiment the CpG-site is within a promoter nucleic acid.

The term "nucleic acid" as used herein, is a polymer consisting of individual nucleotides, i.e. a polynucleotide. It refers to a naturally occurring, or partially or fully non-naturally occurring nucleic acid, which is e.g. encoding a polypeptide that can be produced recombinantly. The nucleic acid can be build up of DNA-fragments which are either isolated or synthesized by chemical means. The nucleic acid can be integrated into another nucleic acid, e.g. in an expression plasmid or the genome/chromosome of a host cell. Plasmid includes shuttle and expression vectors. Typically, the plasmid will also comprise a prokaryotic propagation unit comprising an origin of replication (e.g. the ColE1 origin of replication) and a selectable marker (e.g. ampicillin or tetracycline resistance gene) for replication and selection, respectively, of the vector in bacteria.

The term "promoter strength" and grammatical equivalents thereof as used within the current invention denotes the efficacy of a promoter in the transcription of an operably linked nucleic acid. The promoter strength of a promoter can be high, i.e. it can be of from 75% to more than 100%, or medium, i.e. it can be of from 40% to less than 75%, or low, i.e. it can be up to less than 40%, if compared to the promoter strength of the wild-type hCMV-MIE promoter of SEQ ID NO: 01. This value can be determined by comparing the amount of expression of a heterologous polypeptide operably linked to the promoter in question to the amount of expression of the heterologous polypeptide operably linked to the wild-type SV40 promoter in the same cell type. This can be done e.g. by determining the amount of expression of the heterologous polypeptide in a CHO- or HEK-cell transfected with an expression cassette consisting of the promoter in question operably linked to a nucleic acid encoding the heterologous polypeptide by an ELISA-assay. By comparing this amount to the amount of expression of the same heterologous polypeptide in the same cell line transfected with an expression cassette consisting of the wild-type SV40 promoter operably linked to a nucleic acid encoding the heterologous polypeptide determined with the same ELISA-assay i.e. comparing the amount of heterologous polypeptide in the same cell with the same expression plasmid wherein only the promoter is changed, the relative promoter strength can be determined.

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate the transcription of the linked coding sequence. Generally, but not necessarily, the DNA sequences that are "operably linked" are contiguous and, where necessary to join two protein encoding regions such as a secretory leader/signal sequence and a polypeptide, contiguous and in reading frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within, or downstream of coding sequences, and at considerable distance from the promoter. A polyadenylation site is operably linked to a coding sequence if it is located at the downstream end of the coding sequence in such a way that transcription proceeds through the coding sequence into the polyadenylation sequence. Linking is accomplished by recombinant methods known in the art, e.g., using PCR methodology, and/or by ligation at convenient restriction sites. If convenient restriction sites do not exist, then synthetic oligonucleotide adaptors or linkers are used in accord with conventional practice.

Within the scope of the present invention, transfected cells may be obtained with substantially any kind of transfection method known in the art. For example, the nucleic acid may be introduced into the cells by means of electroporation or microinjection. Alternatively, lipofection reagents such as FUGENE 6 (Roche Diagnostics GmbH, Germany), X-TREMEGENE (Roche Diagnostics GmbH, Germany), and LIPOFECTAMINE (Invitrogen Corp., USA) may be used. Still alternatively, the nucleic acid may be introduced into the cell by appropriate viral vector systems based on retroviruses, lentiviruses, adenoviruses, or adeno-associated viruses (Singer, O., Proc. Natl. Acad. Sci. USA 101 (2004) 5313-5314).

The term "cell" or "host cell" refers to a cell into which a nucleic acid, e.g. encoding a heterologous polypeptide or constituting an shRNA, can be or is introduced/transfected. Host cells include both prokaryotic cells, which are used for propagation of vectors/plasmids, and eukaryotic cells, which are used for the expression of the nucleic acid. In one embodiment the eukaryotic cells are mammalian cells. In another embodiment the mammalian host cell is selected from the mammalian cells comprising CHO cells (e.g. CHO K1 or CHO DG44), BHK cells, NS0 cells, SP2/0 cells, HEK 293 cells, HEK 293 EBNA cells, PER.C6 cells, and COS cells. In a further embodiment the mammalian cell is selected from the group comprising hybridoma, myeloma, and rodent cells. Myeloma cells comprise rat myeloma cells (e.g. YB2), and mouse myeloma cells (e.g. NS0, SP2/0). Polypeptides for use in pharmaceutical applications are in one embodiment produced in mammalian cells such as CHO cells, NS0 cells, Sp2/0 cells, COS cells, HEK cells, BHK cells, PER.C6® cells, or the like. For the fermentation of the host cell and thus for the expression of the polypeptide of interest a cultivation medium is used. Today CHO cells are widely used for the expression of pharmaceutical polypeptides, either at small scale in the laboratory or at large scale in production processes. Due to their wide distribution and use the characteristic properties and the genetic background of CHO cells is well known. Therefore, CHO cells are approved by regulatory authorities for the production of therapeutic proteins for application to human beings. In one embodiment the mammalian cell is a CHO cell.

An "expression cassette" refers to a nucleic acid that contains the elements necessary for expression and secretion of at least the contained structural gene in a host cell. A nucleic acid is likewise characterized by its sequence consisting of individual nucleotides or by the amino acid sequence encoded by the nucleic acid molecule.

A "gene" denotes a nucleic acid which is a segment e.g. on a chromosome or on a plasmid which can effect the expression of a peptide, polypeptide, or protein. Beside the coding region, i.e. the structural gene, a gene comprises other functional elements e.g. a signal sequence, promoter(s), introns, and/or terminators.

A "structural gene" denotes the region of a gene without a signal sequence, i.e. the coding region.

The term "expression" as used herein refers to transcription and/or translation occurring within a cell. The level of transcription of a desired product in a host cell can be determined on the basis of the amount of corresponding mRNA that is present in the cell. For example, mRNA transcribed from a selected nucleic acid can be quantitated by PCR or by Northern hybridization (see Sambrook, et al., Molecular Cloning: A Laboratory Manual, Cold Spring Harbor Laboratory Press (1989)). The protein encoded by a selected nucleic acid can be quantitated by various methods, e.g. by ELISA, by assaying for the biological activity of the protein, or by employing assays that are independent of such activity, such as Western blotting or radioimmunoassay, by using antibodies that recognize and bind to the protein (see Sambrook, et al., 1989, supra).

A "polypeptide" is a polymer of amino acid residues joined by peptide bonds, whether produced naturally or synthetically. Polypeptides of less than about 20 amino acid residues may be referred to as "peptides." Polypeptides comprising two or more amino acid chains or comprising an amino acid chain of a length of 100 amino acids or more may be referred to as "proteins". A polypeptide or protein may also comprise non-peptidic components, such as carbohydrate groups or metal ions. Carbohydrates and other non-peptidic substituents may be added to a protein by the cell in which the protein is produced, and may vary with the type of cell. Proteins and polypeptides are defined herein in terms of their amino acid backbone structure; additions such as carbohydrate groups are generally not specified, but may be present nonetheless. In one embodiment the polypeptide is an immunoglobulin, or an immunoglobulin-fragment, or an immunoglobulin-conjugate. In one embodiment the polypeptide is an immunoglobulin heavy chain or an immunoglobulin light chain or a fragment, fusion or conjugate thereof.

The term "selectable marker" denotes a nucleic acid that allows cells carrying this nucleic acid to be specifically selected for or against, in the presence of a corresponding "selection agent". A useful positive selectable marker is e.g. an antibiotic resistance gene. The selectable marker allows a cell which is transformed therewith to be selected for in the presence of the corresponding selection agent; a non-transformed cell is not capable to grow or survive under selective culture conditions, i.e. in the presence of the selection agent. Selectable markers can be positive, negative or bifunctional. Positive selectable markers allow the selection of cells carrying the marker, whereas negative selectable markers allow cells carrying the marker to be selectively eliminated. Typically, a selectable marker will confer resistance to a drug or compensate for a metabolic or catabolic defect in the cell. Selectable markers useful with eukaryotic cells include, e.g., the genes for aminoglycoside phosphotransferase (APH), such as the hygromycin phosphotransferase (HYG), neomycin and G418 APH, dihydrofolate reductase (DHFR), thymidine kinase (TK), glutamine synthetase (GS), asparagine synthetase, tryptophan synthetase (selection agent indole), histidinol dehydrogenase (selection agent histidinol D), and genes providing resistance to puromycin, bleomycin, phleomycin, chloramphenicol, Zeocin, and mycophenolic acid. Further selectable markers are reported in WO 92/08796 and WO 94/28143.

The term "under conditions suitable for the expression of said polypeptide" denotes conditions which are used for the cultivation of a mammalian cell expressing a heterologous polypeptide and which are known to or can easily be determined by a person skilled in the art. It is also known to a person skilled in the art that these conditions may vary depending on the type of mammalian cell cultivated and type of protein expressed. In general the mammalian cell is cultivated at a temperature, e.g. between 20° C. and 40° C., and for a period of time sufficient to allow effective protein production, e.g. for 4 to 28 days, in a volume of from 0.1 liter to $10^7$ liter.

The term "recovering of the polypeptide" as used within the current application denotes precipitation, salting out, ultrafiltration, diafiltration, lyophilization, solvent volume reduction to obtain a concentrated solution, or chromatography. Generally chromatographic processes are used for the separation and purification of polypeptides. Different methods are well established and widespread used for protein recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The term "immunoglobulin" denotes a molecule comprising at least two so called light chain polypeptides (light chain) and two so called heavy chain polypeptides (heavy chain). Each of the heavy and light chain polypeptides comprises a variable domain (variable region) (generally the amino terminal portion of the polypeptide chain) comprising binding regions that are able to interact with an antigen. Each of the heavy and light chain polypeptides also comprises a constant region (generally the carboxy-terminal portion). The constant region of the heavy chain mediates the binding of the immunoglobulin i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q).

The term "immunoglobulin" herein is used in the broadest sense and encompasses various immunoglobulin structures, including but not limited to monoclonal antibodies, polyclonal antibodies, multispecific antibodies (e.g., bispecific antibodies), and immunoglobulin fragments so long as they exhibit the desired antigen-binding activity.

Depending on the amino acid sequence of the constant region of the heavy chains, immunoglobulins are divided in different classes: IgA class, IgD class, IgE class, IgG class, and IgM class. Some of these classes are further divided into subclasses (isotypes), i.e. IgG in IgG1, IgG2, IgG3, and IgG4, or IgA in IgA1 and IgA2. According to the class to which an immunoglobulin belongs the heavy chain constant regions are called α (IgA), δ (IgD), ε (IgE), γ (IgG), and μ (IgM), respectively. In one embodiment the immunoglobulin is an immunoglobulin of the IgG class. In another embodiment the immunoglobulin has a human constant region or a constant region derived from human origin. In a further embodiment the immunoglobulin is of the IgG4 subclass or the IgG1, IgG2, or IgG3 subclass, which is modified in such a way that no Fcγ receptor (e.g. FcγRIIIa) binding and/or no C1q binding can be detected. In one embodiment the immunoglobulin is of the human IgG4 subclass or a mutated human IgG1 subclass. In one embodiment the immunoglobulin is of the human IgG1 subclass with mutations L234A and L235A. In another embodiment the immunoglobulin is in regard to Fcγ receptor binding of IgG4 subclass or of IgG1 or IgG2 subclass, with a mutation in L234, L235, and/or D265, and/or contains the PVA236 mutation. In a further embodiment the immunoglobulin has a mutation selected from S228P, L234A, L235A, L235E, SPLE (S228P and L235E), and/or PVA236 (PVA236 means that the amino acid sequence ELLG (given in one letter amino acid code) from amino acid position 233 to 236 of IgG1 or EFLG of IgG4 is replaced by PVA). In one embodiment the immunoglobulin is of the IgG4 subclass and has the mutation S228P of IgG4, or the immunoglobulin is of the IgG1 subclass and has the mutations L234A and L235A.

The variable domain of an immunoglobulin's light or heavy chain in turn comprises different segments, i.e. four framework regions (FR) and three hypervariable regions (CDR).

An "immunoglobulin fragment" denotes a polypeptide comprising at least one domain of the group of domains comprising the variable domain, the $C_H1$ domain, the hinge-region, the $C_H2$ domain, the $C_H3$ domain, the $C_H4$ domain of a heavy chain of an immunoglobulin or the variable domain or the $C_L$ domain of a light chain of an immunoglobulin. Also comprised are derivatives and variants thereof. Additionally a variable domain, in which one or more amino acids or amino acid regions are deleted, may be present.

An "immunoglobulin conjugate" denotes a polypeptide comprising at least one domain of an immunoglobulin heavy or light chain conjugated via a peptide bond to a further polypeptide. The further polypeptide is a non-immunoglobulin peptide, such as a hormone, growth receptor, antifusogenic peptide or the like.

The following examples, figures and sequence listing are provided to aid the understanding of the present invention, the true scope of which is set forth in the appended claims. It is understood that modifications can be made in the procedures set forth without departing from the spirit of the invention.

Description of the Sequence Listing

SEQ ID NO: 01 Nucleotide sequence of human CMV major immediate-early (hCMV-MIE) promoter/enhancer SEQ ID NO: 02 Nucleotide sequence of hCMV-MIE promoter/enhancer with C to G point mutation at position −41 relative to the transcription start site SEQ ID NO: 03 Nucleotide sequence of hCMV-MIE promoter/enhancer with C to G point mutation at position −179 relative to the transcription start site SEQ ID NO: 04 Nucleotide sequence of Enhanced Green Fluorescent Protein (eGFP) including a destabilizing PEST sequence SEQ ID NO: 05 Nucleotide sequence of secreted alkaline phosphatase (SEAP) including a signal peptide.

SEQ ID NO: 06 Nucleotide sequence of hCMV-MIE promoter/enhancer with C to G point mutation at position −41 and −179 relative to the transcription start site

EXAMPLE 1

General Techniques
Recombinant DNA Techniques
Standard methods were used to manipulate DNA as described in Sambrook et al.,
Molecular Cloning: A Laboratory Manual, Second Edition, Cold Spring Harbor Laboratory Press, Cold Spring Harbor, N.Y., (1989). The molecular biological reagents were used according to the manufacturer's instructions.
DNA Sequence Determination
DNA sequencing was performed at SequiServe GmbH (Vaterstetten, Germany).
DNA and Protein Sequence Analysis and Sequence Data Management
The EMBOSS (European Molecular Biology Open Software Suite) software package and Invitrogen's Vector NTI version 9.1 were used for sequence creation, mapping, analysis, annotation and illustration.
Sample Preparation for Antibody Analysis:
Cell concentration was calculated and 2 ml per sample were centrifuged (500 g, 5 minutes at 20-30° C.). Supernatant was transferred to new 96 deep well plates and stored at −20° C. until use. Frozen supernatant was thawed overnight at 4° C., 6× inverted and centrifuged (4000 rpm, 30 minutes at 20-30° C.). 310 μl were filtered with a multiscreen Millipore plate atop a barcoded 96 roundwell plate by centrifugation (1200 rpm, 3 minutes at 20-30° C.).

EXAMPLE 2

Figure 2:
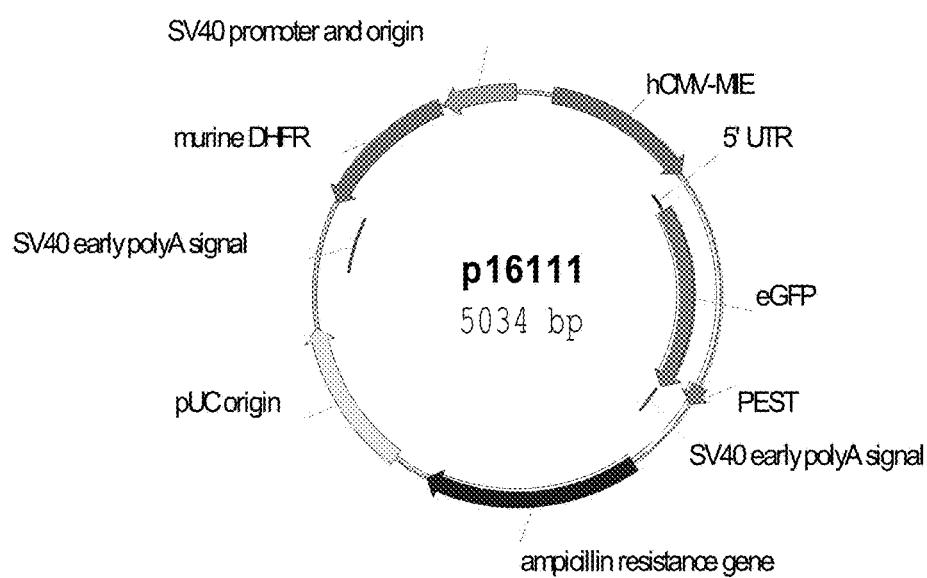
FIG. 2 Plasmid map of Enhanced Green Fluorescent Protein (eGFP) expressing plasmid p16111
Figure 9:
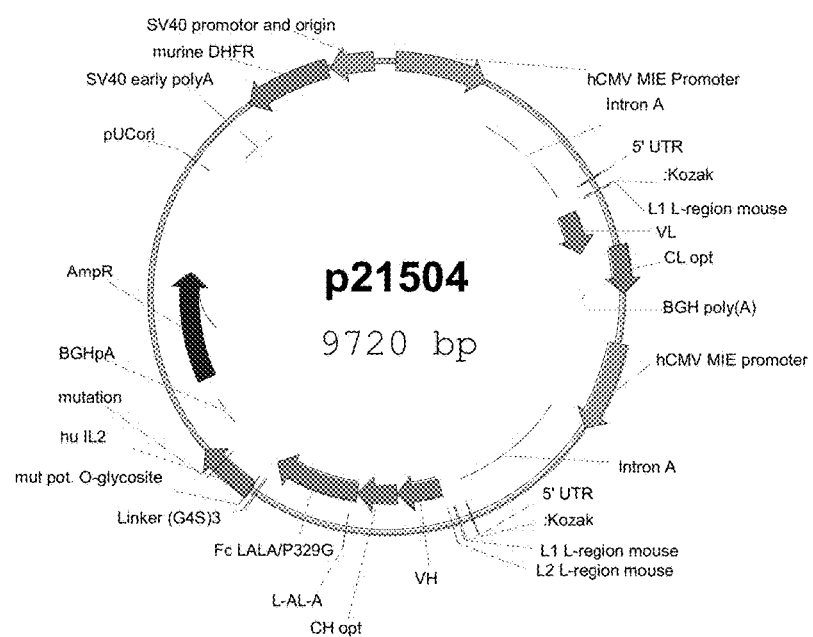
FIG. 9 Plasmid map of IgG class antibody expressing plasmid p21504

Generation of Recombinant CHO Cell Lines
CHO-K1 suspension cells were transfected, either transiently or stably with a vector carrying a reporter gene, either Secreted Alkaline Phosphatase (SEAP: FIG. 1; SEQ ID NO: 05) or enhanced Green Fluorescence Protein (eGFP: FIG. 2) or human antibody constructs of class IgG (IgG cytokine (IL2) fusion protein as reported in WO 2014023752; FIG. 9) under control of a human CMV major immediate-early promoter/enhancer fragment, either wild-type (SEQ ID NO:01) or comprising C to G point mutations. The C to G mutations C-508, C-179 and C-41 of CpG dinucleotides within the hCMV-MIE fragment were inserted alone or in various combinations to increase long term stability (Table 1). The C to G mutations are identified by their distance to the transcription start site (TSS). The mutations were inserted with QuikChange Multi-Site-Directed Mutagnesis Kit (Agilent Technologies, Waldbronn, Germany). The vector further comprised a nucleic acid sequence encoding murine dihydrofolate reductase (DHFR) (FIGS. 1, 2 and 9). Transfection of cells was performed by Amaxa nucleofection system (Lonza Cologne GmbH, Cologne, Germany).

Stably transfected cell suspensions were seeded in 384 or 6-well plates containing thymidine-free medium with 250 to 1600 nM methotrexate (MTX) as selection agent. After three to four weeks, eGFP-expressing cell pools or antibody-expressing cell pools were examined for long term stability over a period of 1-3 month. Intensity of eGFP expression

TABLE 1

Combinations of C to G point mutations of CpG dinucleotides within the human CMV major immediate-early promoter/enhancer fragment C to G point mutations in human CMV major immediate-early promoter/enhancer fragments of SEAP expressing plasmids

| Plasmid NO.: | Code of point mutations | Name of point mutations | Position upstream of transcription start site |
|---|---|---|---|
| 16100 | GGG | C-508, C-179, C-41 | 508, 179, 41 |
| 16101 | GCG | C-508, C-41 | 508, 41 |
| 16102 | CGC | C-179 | 179 |
| 16103 | GCC | C-508 | 508 |
| 16104 | CCG | C-41 | 41 |
| 5532 | CCC | No mutation | |

C to G point mutations in human CMV major immediate-early promoter/enhancer fragments of eGFP expressing plasmids

| Plasmid NO.: | Code of point mutations | Name of point mutations | Position upstream of TSS | Feature |
|---|---|---|---|---|
| 16105 | GGG | C-508, C-179, C-41 | 508, 179, 41 | Gal4-BD binding sequence UAS upstream of hCMV-MIE |
| 16106 | GCG | C-508, C-41 | 508, 41 | |
| 16107 | CGC | C-179 | 179 | |
| 16108 | GCC | C-508 | 508 | |
| 16109 | CCG | C-41 | 41 | |
| 16111 | CCC | No mutation | | |
| 16110 | CCC | No mutation | | |

C to G point mutations in human CMV-major immediate-early promoter/enhancer fragment of human antibody of class IgG expressing plasmids

| Plasmid NO.: | Code of point mutations | Name of point mutations | Position upstream of transcription start site |
|---|---|---|---|
| 16134 | CGG | C-179, C-41 | 179, 41 |
| 16135 | CGC | C-179 | 179 |
| 16136 | CCG | C-41 | 41 |
| 21504 | CCC | No mutation | |

For example, CHO-K1 cells were transfected with circular plasmid DNA for transient expression of SEAP or with linearized plasmid DNA for stable expression of eGFP or with the appropriate plasmid for stable expression of the IgG class antibody fusion protein, using the Nucleofector device in combination with the Nucleofector Kit V (Lonza Cologne GmbH, Cologne, Germany) according to the manufacturer's protocols. Transiently transfected cell suspensions were seeded in 96 well plates and incubated for 5 days. SEAP concentration was examined in a Tecan-Reader SECTRA-Fluor Plus (Tecan Deutschland GmbH, Crailsheim, Germany) by color change of a chemical reaction.

was examined by flow cytometry. Antibody expressing single cell clones were seeded in 384 and 96 well plates. After three weeks, antibody-expressing cell lines were identified by measuring antibody titers in the culture medium by ELISA. Growing wells were randomly picked and in the interests of long term stability assay cell clones were expanded in higher volumes (3 ml per well in 6 well plates) and antibody concentration was determined by protein A HPLC and ELISA at the end of each passage.

The cells were propagated in disposable 125 ml vented shake flasks under standard humidified conditions (95% rH, 37° C., and 5% to 8% $CO_2$) at a constant agitation rate of 120 rpm/min to 150 rpm/min. Every 3-4 days the cells were split into fresh medium. Density and viability of the cultures were determined using the Cedex HiRes cell counter (Roche Innovates AG, Bielefeld, Germany). Furthermore, standard cell culture techniques were applied as described e.g. in Current Protocols in Cell Biology, Binifacino, J. S. et al. (eds), John Wiley & Sons, Inc., New York (2000).

EXAMPLE 3

Long-term Cultivation and Production

Various CHO cell pools containing CpG point mutations within the human CMV major immediate-early promoter/enhancer fragment (Table 1) obtained according to Example 2 were investigated for long-term productivity.

The cells were tested for production stability for 2 to 3 month after transfection in the presence of selection agent MTX. The cells were continuously cultivated in vented 125 ml shake flasks containing 20-40 ml medium with selection agent and diluted twice a week with fresh medium. Seeding density was 2 to $3 \times 10^5$ cells/ml. Prior to passage viable cell density and viability were determined.

Antibody concentration of the supernatant (antibody titer) was determined by protein A HPLC and ELISA at the end of each passage. From these data, the cell specific productivity (qP) for each passage was calculated using the following formula:

$$qP = \frac{P2 - P1}{(D2 - D1)/2 * \Delta t}$$

qP [pg/cell/d]: cell specific productivity,
$P_1$ [µg/ml]: antibody titer at the beginning of the passage,
$P_2$ [µg/ml]: antibody titer at the end of the passage,
$D_1$ [cells/ml]: viable cell density at the beginning of the passage,
$D_2$ [cells/ml]: viable cell density at the end of the passage,
$\Delta t$ [d]: duration of the passage.

The qP values were plotted against the age of culture at the end of the respective passage in generations. A linear trend line was calculated over all qP data points and the relative alteration of the qP (in percent) over the period was calculated in house, according to the following equation:

$$\Delta qP = \frac{m * a}{qP_0 * 100}$$

$\Delta qP$ [%]: percentage alteration of qP,
m [pg/cell/d/generation]: slope of linear trend line,
a [no. of generations]: age of culture,
$qP_0$: y-axis intercept of linear trend line.

In regard to the lower number of data points obtained in the stability assay of hCMV-MIE promoter variants, for each sample the average of the last three qP values was divided by the average of the first two Qp values and displayed in percent to obtain $\Delta qP$.

$$\Delta qP = \frac{\text{average } qP \text{ EOS}}{\text{average } qP \text{ PSB}} * 100$$

Average qP EOS: average of last three qP values
Average qP PSB: average of the first two qP values

EXAMPLE 4

Quantification of Reporter Gene Expression Under Control of Different Human CMV Major Immediate-Early Promoter/Enhancer Fragments.

a) Quantification of SEAP Expression Under Control of Different Human CMV Major Immediate-early Promoter/Enhancer Fragments CHO-K1 cells were transfected with circular plasmid DNA for transient expression of SEAP, using the Nucleofector device in combination with the Nucleofector Kit V (Lonza Cologne GmbH, Cologne, Germany) in the Amaxa Shuttle 96 well plate according to the manufacturer's protocols. 12 transient transfected cell suspensions per plasmid were seeded in 96 well plates and incubated for 5 days. At day 2, 5'-Aza-2'-Deoxycitidine (DAC) was added in 4 replicates per plasmid to a final conc. of 1 µM to demethylate DNA. SEAP concentration was examined Tecan-Reader SECTRAFluor Plus (Tecan Deutschland GmbH, Crailsheim, Germany).

Relative concentration of SEAP was examined by the metabolic rate of pNPP (para-nitrophenylphosphate) to pNP (para-Nitrophenole) according to following protocol:

TABLE 2

Solutions for SEAP Assay:

| Diluent | |
|---|---|
| $MgCl_2*6H_2O$ (Sigma, Cat. No. HM2670-500g MW = 203.31 g/mol) | 100 µl 1M $MgCl_2*6H_2O$ |
| L-homoarginine-HCl (Sigma, Cat. No H1007-5G, MW 224.69 g/mol) | 224.69 mg |
| Diethanolamine (Sigma, Cat. No. D-8885, min. 98%, MW 105.1 g/mol, conc. 1.1 g/ml) | 9.75 ml diethanolamine |
| | adjust to pH 9.8 with concentrated HCL and add $H_2O$ to a final volume of 100 mL |
| Substrate solution | |
| pNPP (4-Nitrophenylphosphate, Roche, Cat. No. 107905, Lot. No. 10030536 | 74.2 mg in 10 ml $H_2O$ |

Figure 3:
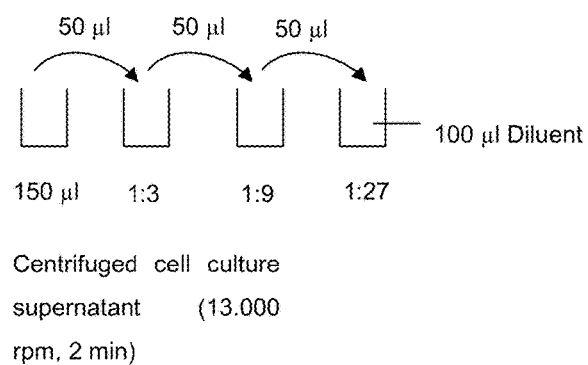
FIG. 3 Procedure of dilution of cell culture supernatant

150 µl of centrifuged cell culture supernatant was diluted 1:3 in multiple steps (FIG. 3).

50 µl dilutions were added in new 96 well plate and combined with 50 µl substrate solution. After 5 minutes, the optical density at 405 nm wavelength was measured using a SECTRAFluor Plus photometer (Tecan Deutschland GmbH, Crailsheim, Germany).

Figure 4:
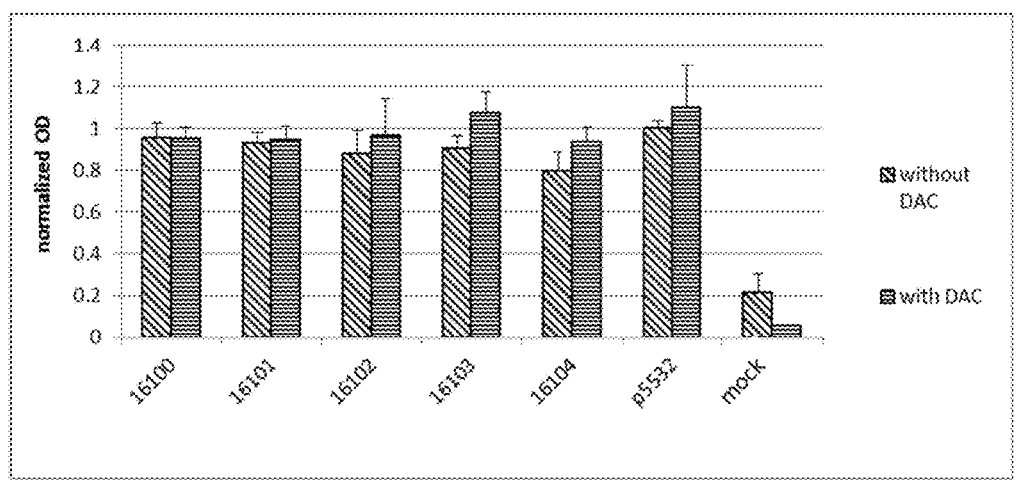
FIG. 4 Normalized SEAP expression levels of transiently transfected CHO cell suspensions without (diagonally shaded columns) or with DAC treatment (vertically shaded columns). The plasmids that were used for transfection are indicated. Error bars represent the standard deviations of eight (without DAC) or 4 (with DAC) biological replicates. The background signal of mock transfected CHO-K1 cells (two biological replicates) is shown also.
Figure 5:
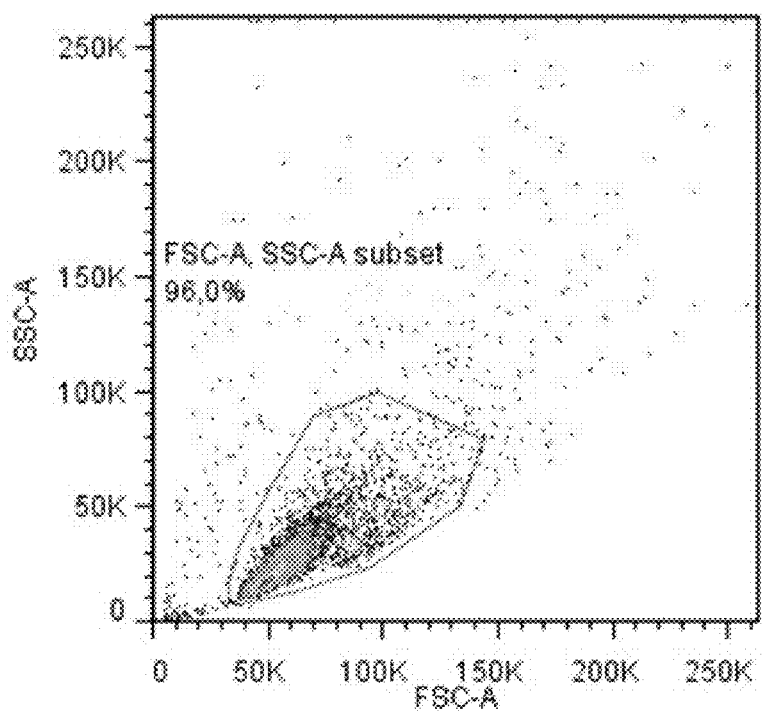
FIG. 5 Living gate of untransfected CHO-K1 cells in the forward scatter (FSC)/side scatter (SSC) dot plot. The same gate was applied to all samples of the same FACS assay.

The average of 8 replicates per plasmid without DAC treatment and the average of 4 replicates per plasmid (Table 1) with DAC treatment were normalized to control plasmid (p5532) without point mutations (FIG. 4).

No significant differences between plasmids with point mutation in human CMV major immediate-early promoter/enhancer fragment and the unmutated control plasmid 5532 were detected. Furthermore no significant difference between samples with and without DAC treatment were observed indicating that no significant promoter silencing occurred within 5 days after transfection. Therefore it is concluded that the point mutations that were introduced into the human CMV major immediate-early promoter/enhancer fragment do not affect promoter strength (point mutations have no influence on the direct potency of human CMV immediate-early promoter/enhancer fragment).

b) Quantification of eGFP Expression Under the Control of Different Human CMV Major Immediate-early Promoter/Enhancer Fragments by FACS Stably transfected cell suspensions expressing eGFP were cultivated over a period of 1-3 months. The intensity of eGFP expression was measured using BD FACS Canto II or BD FACS Calibur (BD, Heidelberg, Germany). Data collection was performed using BD FACS Diva Software v6.12 or Cell Quest Pro Software (BD, Heidelberg, Germany).

Primary data analysis was performed with FlowJo 7.6.5 EN software (TreeStar, Olten, Switzerland).

Figure 6:
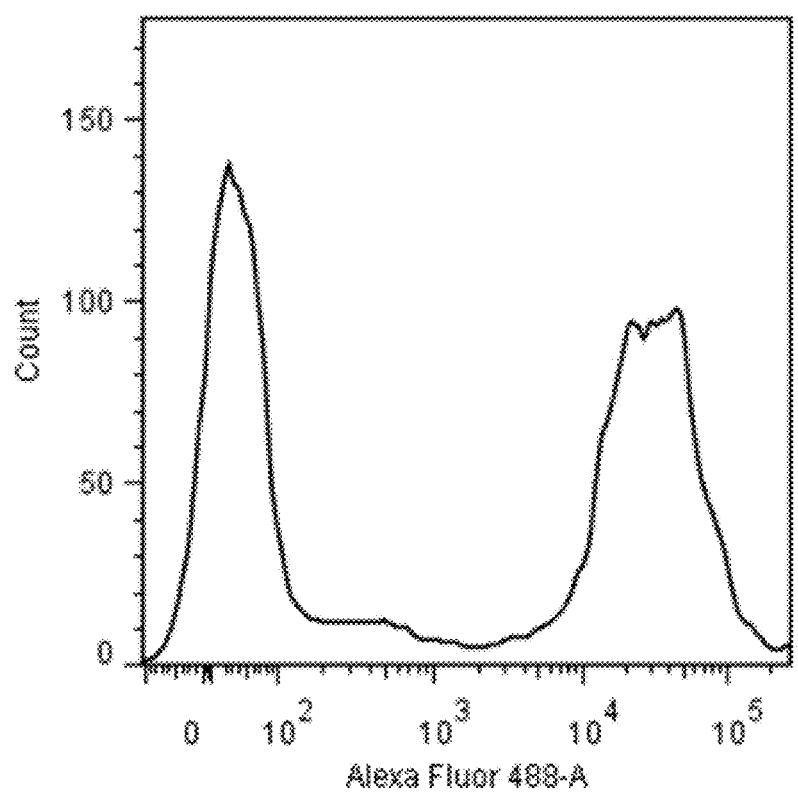
FIG. 6 Living Gate histogram of eGFP fluorescence by a culture of stably transfected CHO cells. Fluorescence was measured at excitation wavelength 488 nm with the Alexa Fluor 488 channel. Two peaks can be discriminated representing the two main subpopulation of non-eGFP expressors (left peak) and high eGFP expressors (right peak).
Figure 8:
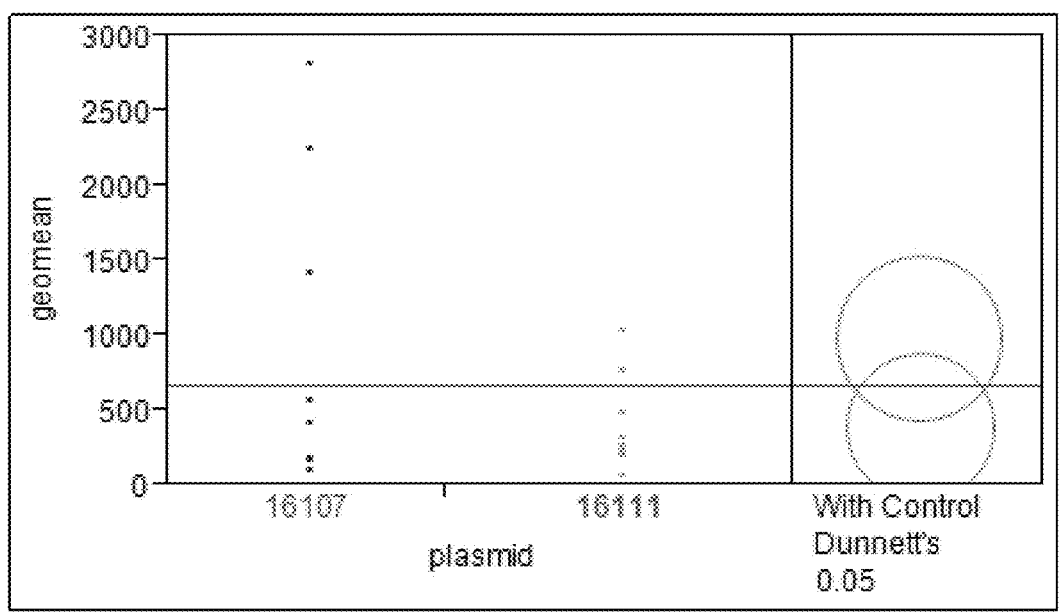
FIG. 8 eGFP expression levels of independent pools of CHO cells six weeks after stable transfection with either plasmid 16107 or 16111. Dots represent geometrical means of fluorescence intensities of individual CHO pools.

For Example, CHO cell suspensions 16105, 16106, 16107, 16108, 16109, 16110 and 16111 were examined with BD FACS Calibur at multiple time points to detect eGFP expression. All samples were examined in 3-4 biological replicates. 10000 events per sample were measured. The gate for living cells was defined with untransfected CHO-K1 cells and applied to all samples of the same FACS experiment (FIG. 8).

eGFP fluorescence of living cells was measured at an excitation wavelength of 488 nm (Alexa Fluor 488 channel) and an emission wavelength of approximately 516 nm. FIG. 6 shows a histogram of fluorescence intensities of living gate events.

Fluorescence data were analyzed with FlowJo 7.6.5 EN software. Geometrical mean, mean and median of eGFP expression within the living gate were calculated in FlowJo. Further statistical analysis was done with JMP software version 10 (SAS, Böblingen, Germany).

EXAMPLE 5

Correlation of eGFP Expression and C to G Point Mutations of the Human CMV Major Immediate-early Promoter/Enhancer Fragment.

8 (plasmids 16107) or 10 (plasmids 16109 or 16111) pools of stably transfected CHO cells were generated and cultivated as described in example 2. eGFP intensities were measured as described in Example 4.

Figure 7:
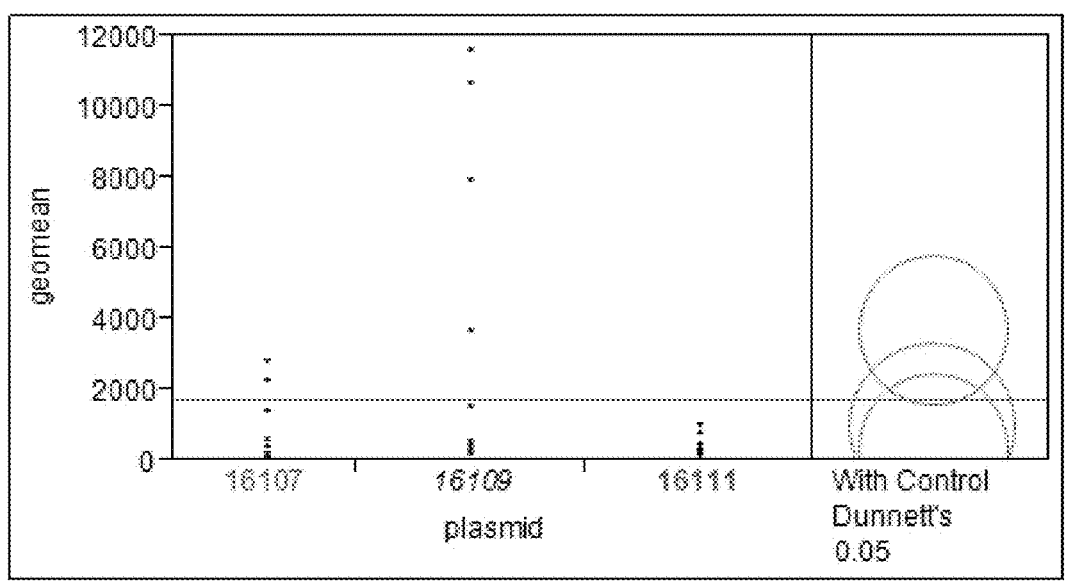
FIG. 7 eGFP expression levels of independent pools of CHO cells six weeks after stable transfection with either plasmid 16107, 16109 or 16111. Dots represent geometrical means of fluorescence intensities of individual CHO pools.

The geometrical means for eGFP intensities were used for correlation studies and displayed in diagrams (FIGS. 7 & 8). To determine significant differences between plasmids 16107 and 16109 as compared to control plasmid 16111 Dunnett's test was used.

P-values of geometrical means of eGFP intensities were calculated for different time points during long-term cultivation (Table 3). The limit for significant difference was set to $p<0.005$.

TABLE 3 p-values of geometrical means of CHO pools transfected with either plasmid 16107, 16109 or 16111

| plasmid | Day of transfection | p-values for LSD of Dunnett's test at date: | | | | | |
|---|---|---|---|---|---|---|---|
| | | Mar. 3 | Mar. 7 | Mar. 14 | Mar. 25 | Apr. 7 | Apr. 25 |
| 16109 | 2014 Jan. 28 | 0.0524 | 0.0244* | 0.0273* | 0.0448* | 0.0812 | 0.1044 |
| 16107 | 2014 Jan. 28 | 0.8759 | 0.8006 | 0.8739 | 0.9792 | 1.0 | 0.9965 |
| 16111 | 2014 Jan. 28 | 1.0 | 1.0 | 1.0 | 1.0 | 1.0 | 1.0 |

For example, significant difference between plasmid 16109 and control plasmid 16111 was detected between 6 weeks and 8 weeks after transfection (sampling days 03-14 to 03-25) (see Table 3). The results of the long-term stability assay combined with the results of the SEAP assay show a positive effect of C to G point mutation C-41 on the stability of reporter gene expression without affecting promoter strength.

Plasmids 16107 and 16111 were pairwise compared in a second calculation. Geometrical means of fluorescence intensities were plotted and p-values were calculated using Dunnett's test (see Table 4).

TABLE 4 p-values of geometrical means of CHO cell lines 16107 and 16111

| plasmid | Day of transfection | p-values for LSD of Dunnett's test at date: | | | | | |
|---|---|---|---|---|---|---|---|
| | | Mar. 3 | Mar. 7 | Mar. 14 | Mar. 25 | Apr. 7 | Apr. 25 |
| 16107 | 2014 Jan. 28 | 0.3898 | 0.1168 | 0.1114 | 0.3250 | 0 9603 | 0.9965 |
| 16111 | 2014 Jan. 28 | 1.0 | 1.0 | 1.0 | 1.0 | 1.0 | 1.0 |

Plasmid 16107 shows increased production stability as compared to control plasmid i.e. C to G point mutation C-179 increases the stability of reporter gene expression without affecting promoter strength.

EXAMPLE 6

Quantification of Antibody Production Under Control of Different Human CMV Major Immediate-early Promoter/Enhancer Fragments a) Quantification of Antibody Production with HPLC:

A chromatographic method was used to quantify the amount of antibody present in a sample. A PorosA column was used that binds the Fc-region of the antibody. The antibody binds to the column and is subsequently eluted by low pH conditions. Protein concentration was established by determining the optical density (OD) at 280 nm, with a reference wavelength of 320 nm, using the molar extinction coefficient calculated on the basis of the amino acid sequence.

b) Quantification of Antibody Production with ELISA:

The ELISA (Enzyme Linked Immunosorbent Assay) technique is based on the antibody sandwich principle. A capture antibody specific to the analyte of interest for instance the Fc part of IgG is bound to a microtiter plate (Maxisorp, Inhouse, Roche) to create the solid phase. Following the blocking and washing steps, samples, standards (dilution series of reference Ab), and controls are then incubated with the solid phase antibody, which captures the analyte. After washing away unbound analyte, a conjugated detection antibody (e.g. POD conjugated) is added. This detection antibody binds to a different epitope of the molecule being measured, completing the sandwich. The BM Chemiluminescence ELISA Substrate POD (Roche, Penzberg, Germany) provides a substrate solution of peroxidase-based (POD, HRP) secondary detection system. The rate of signal generation in an immunoassay is directly proportional to the amount of marker enzyme bound to the solid phase.

EXAMPLE 7

Correlation of Antibody Production/Titer and C to G Point Mutations of the Human CMV Major Immediate-early Promoter/Enhancer Fragment.

Figure 10:
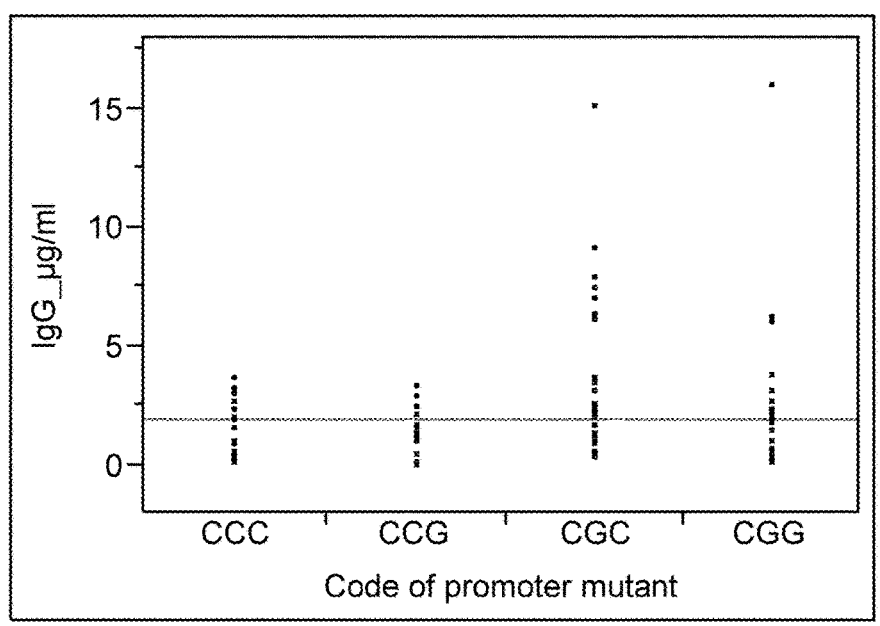
FIG. 10 Antibody titer (μg/ml) of stable transfected CHO cell pools 68 days after transfection (A) or 134 days after transfection (B) with either plasmid 16134 (CGG), 16135 (CGC) or 16136 (CCG) or 21504 (CCC). Dots represent geometrical means of antibody titer of individual CHO pools.
Figure 10:
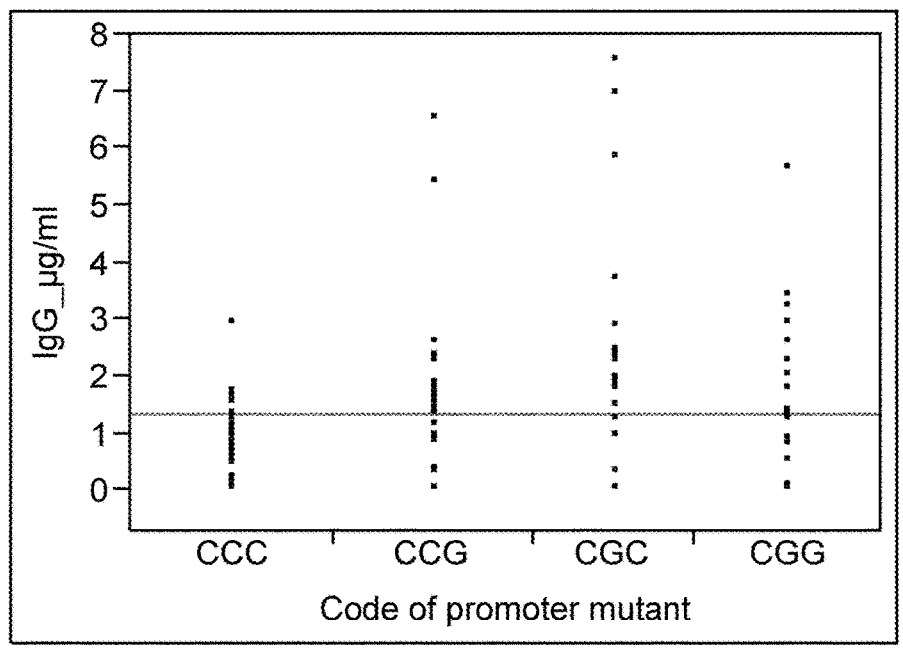

The antibody (IgG-IL2 fusion protein) concentration was examined by using ELISA technology and antibody titer (ug/ml) as well as specific productivity per cell and day (qP) was calculated. Measurements of begin and end of cultivation phase were displayed to visualize difference of mutants to control and alteration of expression during cultivation. Thereby start and end titers of cultivation phase show an improvement of antibody production in all mutants compared to control (FIGS. 10 A and B).

Titers of clonal cell lines were compared with the Tukey HSD test (Table 5). P-values of titer difference of mutated to unmutated promoter variants were calculated. Titers were compared during the cultivation phase. Significance level was set to 0.05 (5%).

TABLE 5

| Days after transfection: | | P-values of Tukey HSD Test, comparing IgG titer of mutants to control. | | | | | |
|---|---|---|---|---|---|---|---|
| | | 68 | 83 | 97 | 124 | 127 | 131 |
| Code of promoter mutant | CCG | 0.993 | 0.964 | 0.936 | 0.946 | 0.999 | 0.986 |
| | CGC | 0.002 | 0.003 | 0.022 | 0.094 | 0.114 | 0.017 |
| | CGG | 0.489 | 0.506 | 0.454 | 0.173 | 0.343 | 0.833 |

For example, CGC mutants were significantly different to control during the whole cultivation phase except day 127 after transfection.

The comparison of titers showed that all mutated cell suspensions had higher antibody productivity per volume than the controls.

It needed to be clarified whether the expression strength or the cell concentration is the main effector of titer difference.

Figure 11:
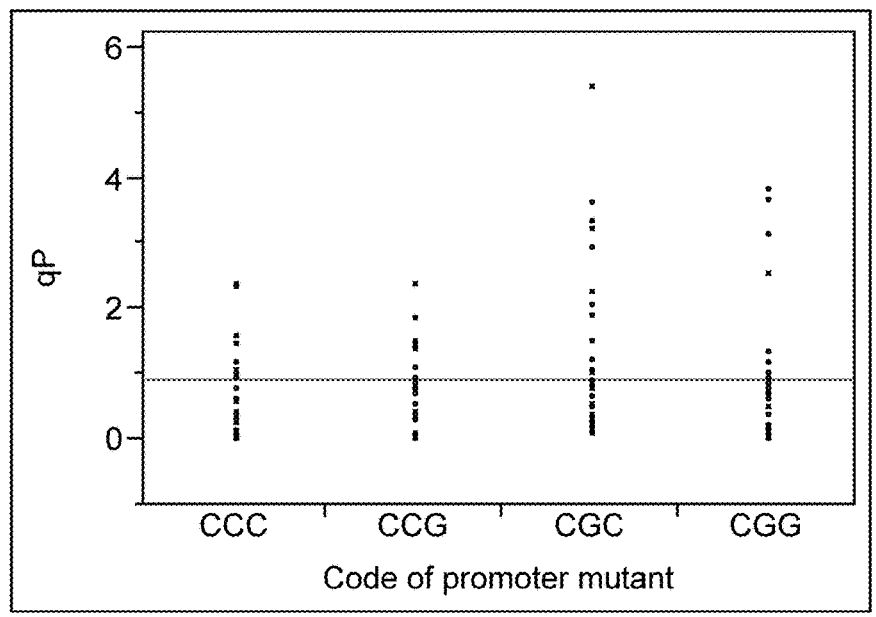
FIG. 11 Specific productivity (qP) of stable transfected CHO cell pools 68 days after transfection (A) or 131 days after transfection (B) with either plasmid 16134 (CGG), 16135 (CGC) or 16136 (CCG) or 21504 (CCC). Dots represent geometrical means of specific productivity of individual CHO pools.
Figure 11:
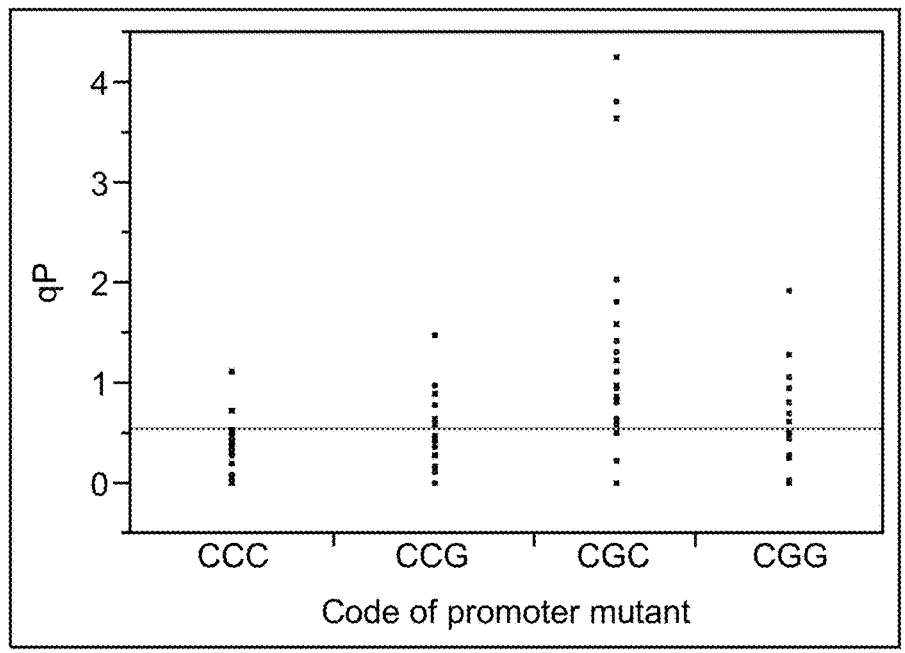

For this purpose the antibody expressions per cell and day (qP) of mutants and control were compared during the whole cultivation phase. The performance of qP values from begin (FIG. 11 A) and end of cultivation phase (FIG. 11 B) were comparable to the titer values with less distinct difference to the control.

Higher titer were obtained for the CGC and the CGG mutant at the begin cultivation. At the end of cultivation CCG and CGG mutants obtained slightly higher qPs than the control. CGC mutated cells had higher qP values at the end of cultivation phase.

The specific productivities of mutated and unmutated cell lines were compared with the Tukey HSD test (Table 6). Thereby the difference of CGC mutants to unmutated control increases over time. Also for CCG mutation an increase of qP values was obtained.

TABLE 6

Tukey HSD Test calculated P-values of hCMV-MIE promoter mutants qPs compared to the unmutated control

| Days after transfection: | | P-values of Tukey HSD Test, comparing qP of mutants to control. | | | | | |
|---|---|---|---|---|---|---|---|
| | | 68 | 83 | 97 | 124 | 127 | 131 |
| Code of promoter mutant | CCG | 0.999 | 0.951 | 0.742 | 0.909 | 0.532 | 1 |
| | CGC | 0.260 | 0.625 | 0.173 | 0.061 | 0.042 | <0.001 |
| | CGG | 0.296 | 0.347 | 0.772 | 0.457 | 0.496 | 0.913 |

Significance level was set to 0.05 (5%).

Taking into account the time dependent increasing difference of qP values for single mutated cell lines compared to unmutated cell lines a higher stability was proposed. To test this hypothesis, the relative alteration of specific productivity was calculated.

At first day and split dependent variation of the specific productivity was stabilized by averaging of the first two (PSB=day 68 & 83) and the last three (EOS=day 124, 127 & 131) qP values. In a second step the alteration of qP was defined as the percentage ratio of stabilized end- to stabilized start-points.

$$\text{relative } \Delta qP = \frac{\text{average } qP\ EOS}{\text{average } qP\ PSB} * 100$$

Figure 12:
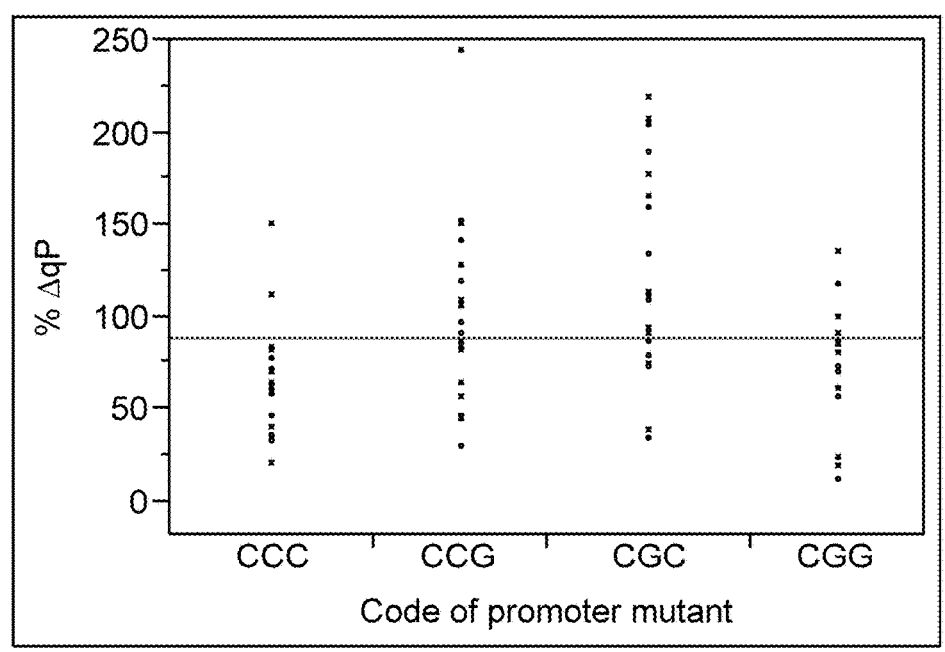
FIG. 12 Comparison of mean with the Tukey HSD test (ΔqP averages) of mutants to control.

Average qP EOS: mean of last three qP's
Average qP PSB: mean of the first two qP's The long term stability of monoclonal cell lines, comprising CGC and CCG promoter mutants, was higher compared to the unmutated control (FIG. 12). The G-41 promoter mutant was stable during the whole cultivation phase, whereas the G-179 point mutation results in an increased IgG expression (mean % ΔqP) over time. The double mutation CGG had high expression values at begin, but decreases over time.

TABLE 7

Comparison of ΔqP averages of mutants to control.
P-values of Tukey HSD test.

| Code of promoter mutant | N | P-values | averages of ΔqP [%] |
|---|---|---|---|
| CGG | 18 | 0.9393 | 71 |

TABLE 7-continued

Comparison of ΔqP averages of mutants to control.
P-values of Tukey HSD test.

| Code of promoter mutant | N | P-values | averages of ΔqP [%] |
|---|---|---|---|
| CGC | 21 | 0.0007 | 118 |
| CCG | 18 | 0.0393 | 101 |
| CCC | 22 | 1 | 63 |

The % ΔqPs of clonal cell lines were compared at a significance level of 0.05 (5%).

Monoclonal cell lines comprising hCMV-MIE promoter variants CGC (16135) and CCG (16136) are significantly more stable than the unmutated control (21504).

The invention claimed is:

1. A promoter comprising the nucleic acid sequence of SEQ ID NO: 02 or SEQ ID NO: 03.

2. A nucleic acid molecule consisting of the nucleic acid sequence of SEQ ID NO: 02 or SEQ ID NO: 03, wherein the nucleic acid molecule is capable of having a promoter strength of at least 80% of the human CMV-major immediate-early promoter of SEQ ID NO: 01 when operably linked to the nucleic acid sequence of SEQ ID NO: 04.

3. A method of producing a polypeptide, comprising:
   a) transfecting a eukaryotic cell with a nucleic acid molecule comprising an expression cassette comprising a first nucleic acid sequence comprising the sequence of SEQ ID NO: 02 or SEQ ID NO: 03 operably linked to a second nucleic acid sequence encoding the polypeptide,
   b) selecting a cell transfected in step a),
   c) cultivating the selected cell of step b) in a cultivation medium, and
   d) recovering the polypeptide from the cell or the cultivation medium, thereby producing the polypeptide.

4. The method according to claim 3, wherein the cultivating is at a final cultivation volume of 500 liters or more.

5. The method according to claim 3, wherein the polypeptide is an immunoglobulin light chain or an immunoglobulin heavy chain or a variant thereof or a fragment thereof or a fusion thereof.

6. The method according to claim 3, wherein the nucleic acid molecule comprises a further expression cassette encoding a selectable marker.

7. The method according to claim 3, wherein said eukaryotic cell is a mammalian cell.

8. The method according to claim 7, wherein said mammalian cell is a CHO cell, a BHK cell, a HEK cell, or a Sp2/0 cell.

9. The method according to claim 8, wherein said mammalian cell is a CHO cell or a HEK cell.

10. The method according to claim 3, wherein said polypeptide is an immunoglobulin, or an immunoglobulin-fragment, or an immunoglobulin-conjugate.

11. The method according to claim 6, wherein said selectable marker is a dihydrofolate reductase, an aminoglycoside phosphotransferase or a hygromycin-phosphotransferase.

12. A cell comprising the promoter according to claim 1.

13. A promoter comprising the sequence of SEQ ID NO: 06.

* * * * *